United States Patent
Schmuck et al.

(10) Patent No.: US 8,491,601 B2
(45) Date of Patent: Jul. 23, 2013

(54) SURGICAL BENDING FORCEPS AND BENDING FORCEPS SYSTEM

(75) Inventors: Manfred Schmuck, Mühlheim-Stetten (DE); Karl Greiner, Mühlheim (DE); Ludger Klein, Freiburg (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 1082 days.

(21) Appl. No.: 11/922,632

(22) PCT Filed: Jun. 22, 2006

(86) PCT No.: PCT/EP2006/006027
§ 371 (c)(1), (2), (4) Date: Feb. 5, 2009

(87) PCT Pub. No.: WO2006/136418
PCT Pub. Date: Dec. 28, 2006

(65) Prior Publication Data
US 2009/0222020 A1    Sep. 3, 2009

(30) Foreign Application Priority Data
Jun. 23, 2005   (DE) .................. 10 2005 029 165

(51) Int. Cl.
*A61B 17/58* (2006.01)
*A61B 17/28* (2006.01)

(52) U.S. Cl.
USPC .......................................... 606/101

(58) Field of Classification Search
USPC .......... 72/213, 380–391.8, 458–461; 606/101, 606/70, 71, 280–299
See application file for complete search history.

(56) References Cited

U.S. PATENT DOCUMENTS

| 275,881 | A | * | 4/1883 | Brastow et al. | ............... | 72/390.6 |
| 4,005,593 | A | * | 2/1977 | Goldberg | ......................... | 72/213 |
| 4,474,046 | A |   | 10/1984 | Cook | | |
| 4,488,425 | A | * | 12/1984 | Meikle | ......................... | 72/389.2 |

(Continued)

FOREIGN PATENT DOCUMENTS

| DE | 172419 | 6/1906 |
| DE | 276067 | 7/1914 |

(Continued)

OTHER PUBLICATIONS

Japanese Publication No. 2003102743 and English language Abstract of Japanese Publication No. 2003102743 from the European Patent Office; 17 pages.

*Primary Examiner* — Kevin T Truong
*Assistant Examiner* — Christopher Beccia
(74) *Attorney, Agent, or Firm* — Howard & Howard Attorneys PLLC

(57) ABSTRACT

Bending forceps (10) for surgical elements such as bone plates (30) are described. The bending forceps (10) have two branches (12, 14) which can pivot relative to one another and with together two counter bearings (26, 28) for the surgical element to be bent. A bending punch (32) for co-operation with the surgical element is provided in a region between the two counter bearings (26, 28). An actuating movement (40) of the branches (12, 14) is converted into a linear movement of the bending punch (32) in the direction of the surgical element by means of an actuating device (40), for example an elliptical linkage gear mechanism.

18 Claims, 3 Drawing Sheets

U.S. PATENT DOCUMENTS

| | | | | |
|---|---|---|---|---|
| 5,113,685 | A | * | 5/1992 | Asher et al. ..................... 72/458 |
| 5,490,409 | A | * | 2/1996 | Weber .............................. 72/458 |
| 5,564,302 | A | * | 10/1996 | Watrous ........................... 72/458 |
| 5,651,283 | A | * | 7/1997 | Runciman et al. ............ 72/390.4 |
| 6,644,087 | B1 | * | 11/2003 | Ralph et al. ...................... 72/213 |
| 7,454,939 | B2 | * | 11/2008 | Garner et al. .................... 72/218 |
| 7,473,257 | B2 | * | 1/2009 | Knopfle et al. ............... 606/101 |
| 7,488,331 | B2 | * | 2/2009 | Abdelgany .................... 606/109 |
| 7,740,634 | B2 | * | 6/2010 | Orbay et al. .................. 606/101 |

FOREIGN PATENT DOCUMENTS

| | | |
|---|---|---|
| DE | 1087990 | 8/1960 |
| DE | 1914120 | 4/1965 |
| DE | 2850892 A1 | 5/1980 |
| DE | 10301692 A1 | 8/2004 |
| JP | 54034499 U | 3/1979 |
| JP | 2003500154 U | 1/2003 |
| JP | 2003102743 A | 4/2003 |
| WO | 0072767 A1 | 12/2000 |

* cited by examiner

SURGICAL BENDING FORCEPS AND BENDING FORCEPS SYSTEM

CROSS-REFERENCE TO RELATED APPLICATION

The instant application claims priority to and all the advantages of International Patent Application No. PCT/EP2006/006027, filed on Jun. 22, 2006, which claims priority to German Patent Application No. 10 2005 029 165.1, filed on Jun. 23, 2005, the entire specifications of both of which are expressly incorporated herein by reference.

FIELD OF THE INVENTION

The present invention relates to bending forceps for surgical elements, such as are used for example for bending bone plates for the craniomaxillofacial region. The invention also relates to a bending forceps system comprising the bending forceps.

BACKGROUND OF THE INVENTION

As a preliminary to or during a surgical intervention it is often necessary to adapt and match implants and other surgical elements to anatomical circumstances. The anatomical circumstances can be determined for example by the curvature of a bone or the course of a fracture. In order to adapt surgical elements to anatomical circumstances, the surgeon has a wide range of instruments at his disposal. This range of instruments includes for example cutting forceps, bending forceps, plate benders and similar instruments.

From U.S. Pat. No. 4,474,046 three-point bending forceps for surgical rods are known. The bending forceps have two branches that can swivel about a common axis of rotation. A bending punch is provided in the region of the common axis of rotation. Two counter bearings are associated with the bending punch, which are formed on free ends of the branches. When the branches are actuated the bending punch remains fixed and the two counter bearings execute movements on elliptical paths about the bending punch. As a result of these movements a rod arranged between the bending punch and the counter bearings is bent around the bending punch. In order to be able to bend rods of different diameter (or achieve different bending radii), the bending punch has an outer contour that differs from section to section. By rotating the bending punch about the axis of rotation of the branches a desired contour section can be chosen, by means of which the bending punch is to co-operate with the rod to be bent.

U.S. Pat. No. 5,490,409 discloses further three-point bending forceps with a rotatable, eccentrically mounted bending punch. In order to be able to stop the rotatable bending punch with certainty at a desired angular setting, a mechanism is provided with two arms coupled to one another via a joint. A guide pin is arranged in the region of the joint, which pin executes a linear movement when the bending forceps are actuated. At the same time the guide pin slides within a channel formed on the rear side of the bending punch in order to lock the bending punch at a fixed angle.

From U.S. Pat. No. 5,651,283 multifunctional bending forceps for linear bone plates are known. By means of the bending forceps a linear bone plate can be bent in a preferred plane of the bone plate and can also be bent outwardly from the preferred plane. The bending of the bone plate in the preferred plane is effected by means of a three-point mechanism. The three-point mechanism comprises two counter bearings provided in the head region of a first branch, as well as a bending punch that is formed on a mouth section swivellably mounted in the head region of the first branch. The mouth section is coupled via a linkage to a second branch. A connecting arm between the first and the second branch is guided via its first end within a slit formed in the first branch and is linked via its second end to the second branch.

It has been found that the approach known from U.S. Pat. No. 5,651,283, namely to provide the bending punch on a swivellable mouth section, has disadvantages. One disadvantage is for example the fact that the bending punch can be deflected only to a limited extent. On account of this limited deflectability the area of application of the bending forceps is basically limited to bone plates with narrowly defined geometrical dimensions.

From DE 103 01 692 A1 further three-point bending forceps are known. The bending forceps comprise a bending punch which can swivel relative to two counter bearings. In contrast to the bending forceps of U.S. Pat. No. 5,651,283, a sufficient deflectability of the bending punch is ensured, so that bone plates of different geometrical dimensions can be bent. However, during a bending procedure the swivelling movement of the bending punch can have a destabilising effect on the position of the bone plate to be bent.

The object of the present invention is to provide bending forceps for surgical elements such as bone plates, which have a wide area of application and provide a precise bending. A further object of the present invention is to provide a bending forceps system comprising the bending forceps.

SUMMARY OF THE INVENTION

Bending forceps according to the invention for surgical elements comprise two branches which are pivotable relative to one another, which are coupled (for example rigidly or articulatedly) to together at least two first counter bearings, a first bending punch for co-operation with the surgical element in a region between the two first counter bearings, and an actuating device for the first bending punch, which converts an actuating movement of the branches into a linear movement of the first bending punch in the direction of the surgical element.

The actuating device for the first bending punch can be designed so that the first bending punch is movable by means of the actuating device along a (imaginary) straight line. Guide means may optionally be provided, which stabilise the linear movement of the first bending punch.

One possible design of the actuating device includes a gear mechanism for converting the pivotal movement of the branches into the desired linear movement of the bending punch. The gear mechanism can have a gear ratio such that the pivotal movement of the branches results in a comparatively wide axial displacement or misalignment of the first bending punch. This axial displacement is for example more than about 1 cm.

The gear mechanism can be a lever mechanism. In this regard, various realisations are conceivable. For example, the actuating device can be designed in the manner of an elliptical linkage gear mechanism. Examples of elliptical linkage gear mechanisms are described in Chapters 3.4.5.7.1 and 3.4.5.7.2 of the handbook by S. Hildebrand, entitled "Feinmechanische Bauelemente", Karl Hanser Verlag, Munich. The described elliptical linkage gear mechanisms and modifications thereof are capable of converting an actuating movement of the branches into a linear bending punch movement. For this purpose the gear mechanism can be articulatedly coupled to each of the two branches as well as to the bending punch.

In one embodiment of the bending forceps the actuating device (thus for example the elliptical linkage gear mechanism) comprises at least a first lever, which is articulatedly coupled to a first of the two branches and to the first bending punch. The actuating device can furthermore include a second lever, which is articulatedly coupled to the second branch and likewise to the first bending punch. The first and second levers can be coupled to one another and also to the first bending punch by means of a common joint. The common joint is, according to a first variant, formed directly in the region of the first bending punch. According to a second variant the first bending punch is spaced apart from the common joint. For this purpose the bending forceps can include an extension arm with two oppositely facing ends. The first bending punch is conveniently arranged on a first end of the extension arm, while a second end of the extension arm can be articulatedly coupled to the first and to the second levers. The first bending punch can be designed in one piece with the extension arm.

The two first counter bearings can be fixed immovably relative to one another, or can be variably spaced from one another depending on the actuating state of the bending forceps. It is possible to provide both counter bearings on one and the same branch. It would however also be conceivable to form one of the two first counter bearings on each of the two branches.

The first counter bearings or the first bending punch or all these components can be contoured so as to co-operate with a complementary contour of the surgical element. Such a measure has a positionally stabilising effect with regard to the surgical element and accordingly facilitates the bending procedure.

According to a first mode of construction a separate axis of rotation is provided for each of the two pivotable branches. The axes of rotation of the two branches are in this case spaced from one another. According to a second mode of construction both branches can pivot about a common axis of rotation.

In a multifunctional design of the bending forceps, the branches with a common axis of rotation each comprise a second counter bearing for the surgical element. In the region of the common axis of rotation of the branches a second bending punch is formed, which is stationary under an actuating movement of the branches, and is provided for co-operation with the surgical element in a region between the two second counter bearings.

In a modification of these bending forceps a nominal interspacing between the second bending punch and the second counter bearings can be adjusted. To adjust the nominal interspacing the second bending punch can pivot eccentrically and/or can have different contour sections.

The first and second counter bearings and the first and second bending punches can be provided at different positions on one and the same bending forceps. To simplify handling and manipulation, the first counter bearings and the first bending punch are conveniently formed on a first side of the branches, and the second counter bearings and the second bending punch are formed on a second side of the branches opposite the first side.

According to a further aspect according to the invention a bending forceps system is provided for surgical elements such as bone plates. The bending forceps system includes, in addition to the bending forceps, also the surgical element to be bent.

The surgical element, for example a linear bone plate, can have a preferred plane. Accordingly the bending forceps can be designed so as to bend the surgical element in the preferred plane as well as outwardly from the preferred plane. The bending in the preferred plane is expediently effected by means of the first counter bearings and the first bending punch, whereas the second counter bearings and the second bending punch can be used for bending outwardly from the preferred plane. Advantageously suitable bearing surfaces for the surgical element to be bent are formed in the region of the counter bearings and bending punch, in order to be able to appropriately position, according to requirements, the preferred plane of the element relative to the counter bearings and bending punch.

DESCRIPTION OF THE DRAWINGS

Further details and advantages of the invention follow from the following description of an example of implementation, as well as from the figures, in which.

DESCRIPTION OF A PREFERRED EMBODIMENT

The invention is described hereinafter with the aid of an embodiment of multifunctional surgical bending forceps for bone plates. The use of the bending forceps for bending bone plates should obviously be understood only as an example, since the bending forceps are also suitable for bending other surgical elements such as rods or wires, which have no preferred plane. Furthermore it should be pointed out that the example of implementation relates to multifunctional bending forceps with two separate mechanisms, namely on the one hand a mechanism for bending the bone plate in a preferred plane, and on the other hand a mechanism for bending outwardly from the preferred plane. It is understood per se that one of the two mechanisms could also be omitted or modified.

Figure 1:
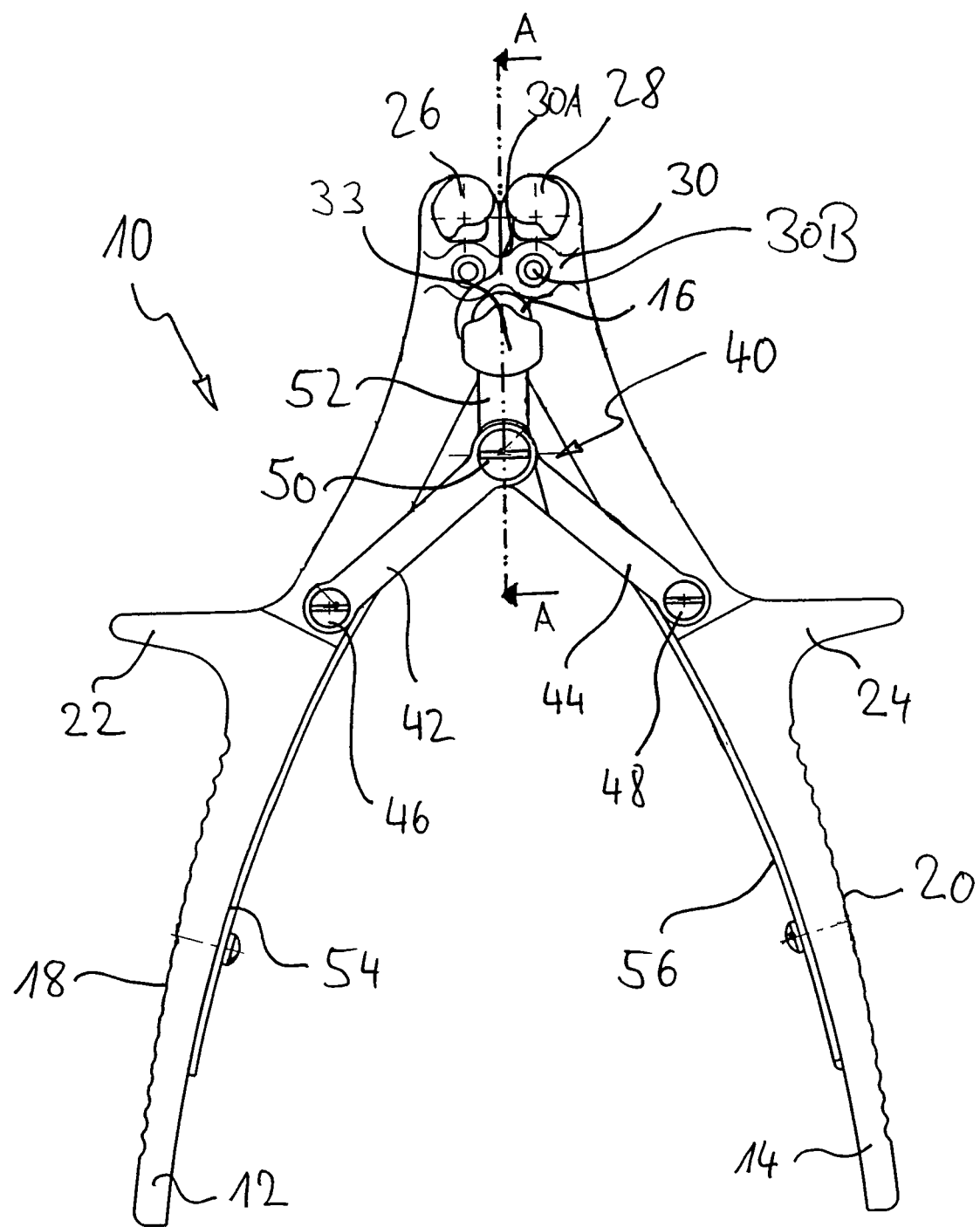
FIG. 1 is a plan view of an embodiment of bending forceps according to the invention.

FIG. 1 shows a front view of bending forceps according to a preferred embodiment, generally identified by the reference numeral 10, with two branches 12, 14. The two branches 12, 14 can in the example of implementation pivot about a common axis of rotation, which in FIG. 1 is defined by a rotation bearing 16. The lower ends of the two branches 12, 14 in FIG. 1 are designed as handles 18, 20. The handles 18, 20 have in each case a structured surface and terminate in the direction of the rotation bearing 16 in each case in an outwardly extending projection 22, 24. The two projections 22, 24 facilitate the manipulation of the bending forceps 10 and, just like the structured surfaces, prevent a surgeon's hand slipping in the direction of the bone plate to be bent. The danger of a hand slipping off would exist in particular if greater actuation forces were necessary in the case of thicker bone plates.

Each of the two branches 12, 14 terminates at its end remote from the respective handle 18, 20, in a roller-like counter bearing 26, 28. In the illustrated embodiment the counter bearings 26, 28 are rigidly coupled to the branches 12, 14 (and to the handles 18, 20). The counter bearings 26, 28 extend outwardly from the plane of the drawing in FIG. 1 (cf. FIG. 3) and have in each case an outer contour roughly in the shape of a droplet. The distance of the two counter bearings 26, 28 from the common axis of rotation of the two branches 12, 14 is significantly shorter than the distance of the two handles 20, 22 from the axis of rotation. The resulting leverage ratios reduce the force required to bend the bone plate 30.

The outer contour of the counter bearings 26, 28 is adapted to the contour of the bone plate to be bent (shown only diagrammatically in FIG. 1 and identified by the reference numeral 30) and is substantially complementary thereto. The contouring has a positionally stabilising effect on the bone plate 30 during a bending operation and accordingly simplifies the manipulation of the bending forceps 10.

Figure 3:
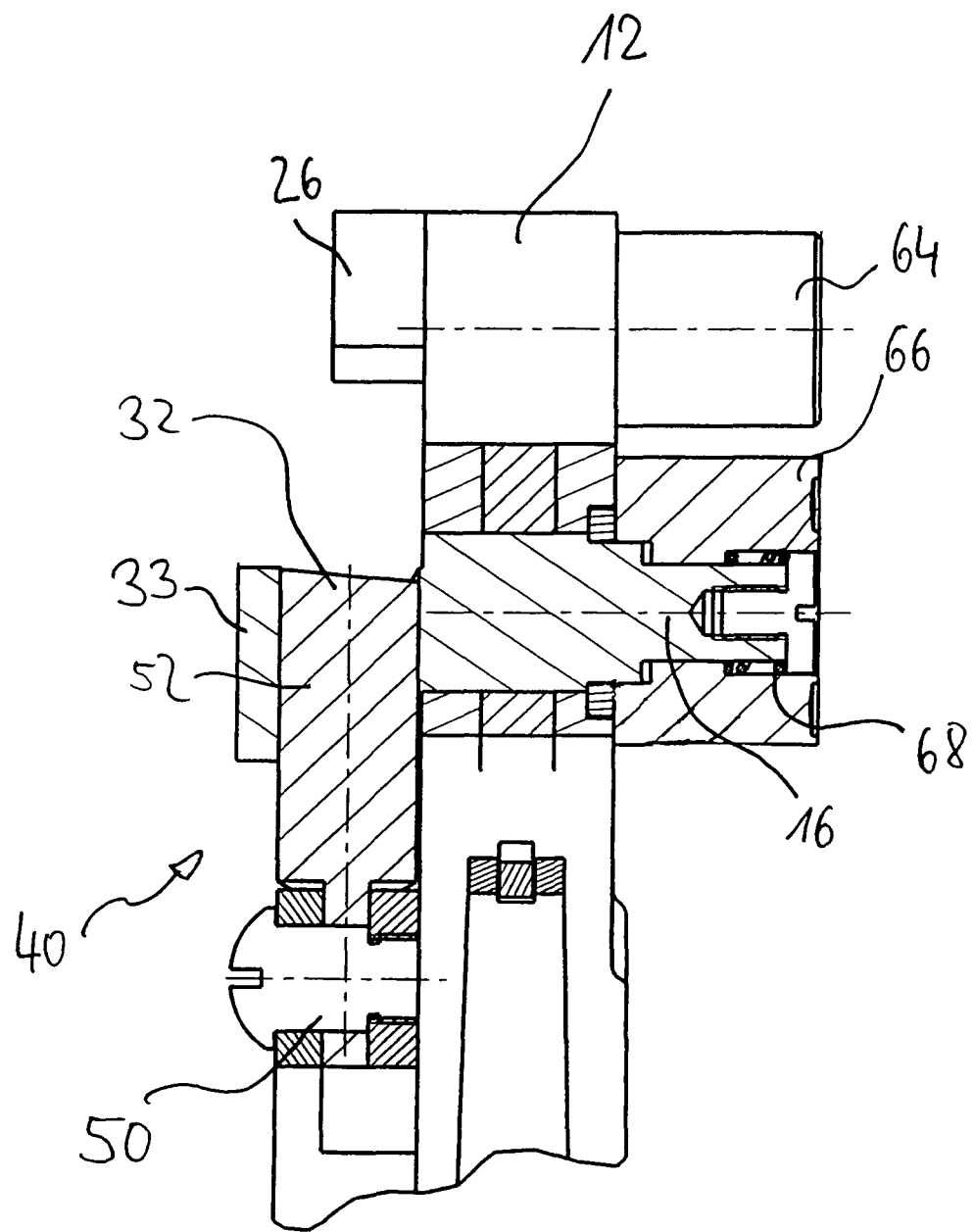
FIG. 3 is a sectional view along the line A-A in FIG. 1

A bending punch 32 is provided in a region between the two counter bearings 26, 28 (and in FIGS. 1 and 3, underneath these counter bearings 26, 28). In FIG. 1 the bending punch 32 is covered by a linear guide 33 for the bending punch 32. The linear guide 33 is in the view according to FIG. 1 contoured in a complementary manner to the bone plate 30. This contouring facilitates the accommodation of the bone plate 30 to be bent.

The bending punch 32 has, like the counter bearings 26, 28, an approximately droplet-shaped outer contour with a bulge (not recognisable in the figures) pointing in the direction of the bending plate 30. It is accordingly likewise contoured in a substantially complementary manner to the bone plate 30 and is designed so as to cooperate with the bone plate 30 in a tapered region 30A (formed between two passage openings 30B for securement elements such as bone screws).

An actuating device 40 is provided for the bending punch 32. The actuating device 40 converts an actuating movement of the two branches 12, 14 into a linear movement of the bending punch 32 in the direction of the two counter bearings 26, 28 and thus also in the direction of the bone plate 30.

The actuating device 40 is designed in the embodiment in the manner of an elliptical linkage gear mechanism, though in contrast to "conventional" elliptical linkage gear mechanisms (cf. the above-mentioned handbook by S. Hildebrand), in the embodiment no fixed anchorage point is provided. The elliptical linkage gear mechanism is instead in the present case coupled to each of the two movable branches 12, 14 and to the bending punch 32 to be actuated.

In the embodiment the actuating device 40 designed as an elliptical linkage gear mechanism includes two equally long levers 42, 44. One lever 42 is coupled via a joint 46 to one branch 12, and the other lever 44 is coupled via a further joint 48 to the other branch 14. At their ends remote from the branches 12, 14 the two levers 42, 44 are coupled by means of a common joint 50 to one another as well as to the bending punch 32. More precisely, the two levers 42, 44 are connected at the common joint 50 to an extension arm 52 carrying the bending punch 32. In the present case the bending punch 32 is formed in one part with the extension arm 52. With an actuating movement of the two branches 12, 14 the extension arm 52 slides along the linear guide 33, so that the linear guide 32 has a stabilising action on the movement of the extension arm 52 and thus also has a stabilising action on the movement of the bending punch 32.

FIG. 1 shows the initial or normal position of the bending forceps 10. In this position the two handles 18, 20 are held apart from one another by leaf springs 54, 56, which are only partly shown in FIG. 1. When actuating the bending forceps 10 the initial tension of the leaf springs 54, 56 consequently has to be overcome.

The front side, illustrated in FIG. 1, of the bending forceps 10 with the bending punch 32 and the two counter bearings 26, 28 is provided so as to bend the bone plate 30 in its preferred plane. To this end, in a first step the bone plate 30 is, as illustrated in FIG. 1, placed flat on the front surface of the bending forceps 10, and more particularly in an intermediate space between the bending punch 32 on the one hand and the two counter bearings 26, 28.

When placing the bone plate 30, this is positioned by the surgeon so that the tapered region 30A is placed centrally with respect to the bulge of the bending punch 32. In this way the bulge-shaped sections of the bone plate 30 are automatically positioned correctly as regards the contoured counter bearings 26, 28. A movement of the branches 12, 14 towards one another then takes place on actuating the branches 12, 14, while overcoming the initial tension of the leaf springs 54, 56.

The actuating movement of the branches 12, 14 is converted by the actuating device 40 into a linear movement of the bending punch 32 in the direction of the bone plate 30. This conversion is due to the fact that the two levers 42, 44 approach one another. As a consequence of this approach movement the common joint 50 of the two levers 42, 44 and thus also of the extension arm 52 for the bending punch 32 coupled to this joint 50, is moved in the direction of the bone plate 30. The resulting movement of the bending punch 32 takes place along the dotted straight line identified by the arrow A.

An advantageous feature of the actuating device 40 according to this embodiment is the fact that the bending punch 32 is guided along a straight line substantially perpendicular to the bone plate 30, and not along an elliptical path. This provides an increased precision of the bending, since no laterally directed (shear) forces occur. It is furthermore advantageous that a comparatively small actuating movement of the branches 12, 14 can be converted into a relatively large linear displacement of the bending punch 32. As a consequence, the nominal distance between the two counter bearings 26, 28 and the bending punch 32 can be maintained relatively large. Accordingly, bone plates 30 of different widths can be positioned between the bending punch 32 and the counter bearings 26, 28 and bent.

It is moreover advantageous that the bending procedure is assisted by the movement of the counter bearings 26, 28 (in each case along an elliptical path). This assistance consists essentially in the fact that the bone plate 30, on account of the movement of the counter bearings 26, 28, is as it were bent around the bending punch 32. As a variant of the example of implementation illustrated in FIGS. 1 to 3, the two counter bearings 26, 28 could of course also be arranged relatively stationary to one another, for example on only one of the two branches 12, 14.

Figure 2:
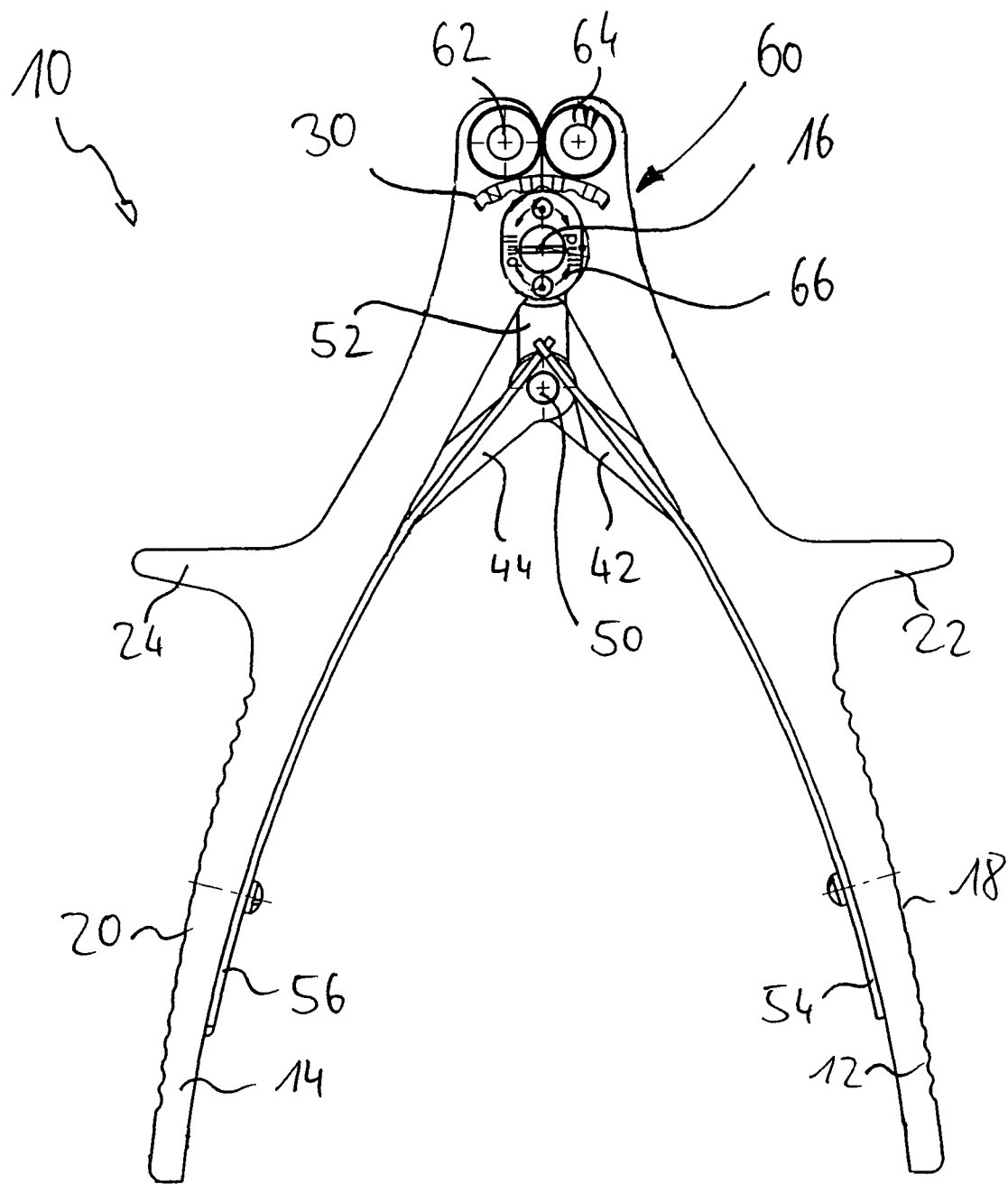
FIG. 2 is a rear view of the bending forceps according to FIG. 1.

FIG. 2 shows a view of the rear side of the bending forceps 10 with a device 60 for bending the bone plate 30, shown simply diagrammatically, from its preferred plane. The device 60 concludes two roller-like counter bearings 62, 64 as well as a bending punch 66. Each of the two counter bearings 62, 64 is formed on an end of the branches 12, 14 remote from the respective handle 18, 20. The counter bearings 62, 64 extend in FIG. 2 outwardly from the plane of the diagram (cf. FIG. 3) and each has a circular outer contour. The distance of the two counter bearings 62, 64 from the common axis of rotation of the two branches 12, 14 is significantly shorter than the distance of the two handles 20, 22 from the axis of rotation. The resulting leverage ratios reduce the force needed to bend the bone plate 30.

The bending punch 66 can rotate relative to the common rotation bearing 16 of the two branches 12, 14. As can be seen from FIG. 2, the bending punch 66 has an elliptical basic shape and is mounted eccentrically with respect to the axis of rotation 16. The eccentric bearing of the bending punch 66 can also be seen in the sectional view according to FIG. 3.

The bending punch 66 can be positioned in two different catch positions with respect to the rotation bearing 16. In the first catch position illustrated in FIGS. 2 and 3, a first distance is adjusted between the end of the bending punch 66 facing towards the bone plate 30 and the ends of the counter bearings 62, 64 facing towards the bone plate 30. The bending punch 66 can be moved from the catch position illustrated in FIGS. 2 and 3 to a second catch position rotated by 180° relative to the axis of rotation of the branches 12, 14. In this second catch position, on account of the eccentric bearing of the bending punch 66 a second distance is adjusted between the bending punch 66 and the two counter bearings 62, 64, which is larger than the first distance mentioned above. The second catch position is therefore suitable in particular for bending thicker bone plates.

In order to move the bending punch 66 from the first catch position to the second catch position (and vice versa), in a first step it is necessary to withdraw the bending punch 66 from the plane of the diagram according to FIG. 2, while overcoming the initial tension of a helical spring 68 (cf. FIG. 3). The withdrawn bending punch 66 is then rotated in a second step by 180°. After the rotation of the bending punch 66 this is released again in a third step, whereupon the helical spring 68 forces the bending punch 66 into the second catch position.

FIG. 2 shows, like FIG. 1, the initial state of the bending forceps 10. In order to bend the bone plate 30 this is first of all positioned, as illustrated in FIG. 2, between on the one hand the counter bearings 62, 64 and on the other hand the bending punch 66, in such a way that the front side of the flat bone plate 30 rests on the surface of the bending forceps 10 (more specifically on the surfaces of the branches 12, 14). The bone plate 30 is thus positioned edgeways. Since the distance between the counter bearings 62, 64 and the bending punch 66 in the initial position illustrated in FIG. 1 is now only slightly larger than the thickness of the bone plate 30, the position of the bone plate 30 is stabilised by the counter bearings 62, 64 and the bending punch 66.

After the positioning of the bone plate the surgeon actuates the branches 12, 14 while overcoming the initial tension of the leaf springs 54, 56 against one another. During this actuating movement of the branches 12, 14 the bending punch 66 remains stationary. The counter bearings 62, 64 move on the other hand along elliptical paths around the bending punch 66. The bone plate 30 positioned between the counter bearings 62, 64 and the bending punch 66 is gripped by this movement of the counter bearings 62, 64 and is thus bent around the bending punch 66. Since the preferred plane of the bone plate 30 is aligned perpendicular to the axis of rotation of the two branches 12, 14, the bone plate 30 is bent out from its preferred plane.

The invention has been discussed with the aid of a preferred embodiment. Numerous changes and modifications are however conceivable. The invention can therefore also be implemented differently from the above illustration, but within the scope of the following claims.

The invention claimed is:

1. Bending forceps for surgical elements, comprising:
   two branches which are pivotable relative to one another and which together comprise two first counter bearings for the surgical element to be bent;
   a first bending punch for co-operation with the surgical element in a region between the two first counter bearings; and
   an actuating device for the first bending punch, which converts an actuating movement of the branches into a linear movement of the first bending punch in a direction towards the surgical element, wherein the two first counter bearings, on the basis of the actuating movement of the branches, move apart from each other.

2. The bending forceps according to claim 1, wherein the actuating device is designed as a gear mechanism.

3. The bending forceps according to claim 2, wherein the gear mechanism is coupled in an articulated manner to each of the branches and to the bending punch.

4. The bending forceps according to claim 1, wherein the actuating device includes:
   at least a first lever, which is coupled in an articulated manner to a first of the branches and to the first bending punch.

5. The bending forceps according to claim 4, wherein the actuating device includes:
   a second lever, which is coupled in an articulated manner to a second of the branches and to the first bending punch.

6. The bending forceps according to claim 5, wherein the first and the second levers are coupled at a common joint to one another and to the first bending punch.

7. The bending forceps according to claim 5, wherein the bending forceps include an extension arm with two oppositely lying ends, wherein the first bending punch is arranged on a first of the ends and a second of the ends is coupled in an articulated manner to the first and second levers.

8. The bending forceps according to claim 1, wherein a linear guide is provided for stabilising the linear movement of the first bending punch.

9. The bending forceps according to claim 1, wherein the first counter bearings are contoured in order to co-operate with a complementary contour of the surgical element.

10. The bending forceps according to claim 1, wherein the two branches are pivotable about a common axis of rotation.

11. The bending forceps according to claim 10, wherein the branches each comprise a second counter bearing for the surgical element, and in the region of the common axis of rotation of the branches a second bending punch is formed which is stationary during an actuation movement of the branches, which is provided for co-operation with the surgical element in a region between the two second counter bearings.

12. The bending forceps according to claim 11, wherein a nominal distance between the second bending punch and the second counter bearings is adjustable.

13. The bending forceps according to claim 11, wherein the first counter bearings and the first bending punch are formed on a first side of the branches and the second counter bearings and the second bending punch are formed on a second side of the branches lying opposite the first side.

14. A bending forceps system for surgical elements, comprising:
   a surgical element to be bent;
   bending forceps comprising two branches which are pivotable relative to one another and which together comprise two first counter bearings for the surgical element to be bent;
   a first bending punch for co-operation with the surgical element in a region between the two first counter bearings; and
   an actuating device for the first bending punch, which converts an actuating movement of the branches into a linear movement of the first bending punch in a direction towards the surgical element, wherein the two first counter bearings, on the basis of the actuating movement of the branches, move apart from each other.

15. The bending forceps system according to claim 14, wherein the surgical element has a preferred plane and the bending forceps are designed so as to bend the surgical element in the preferred plane and also outwardly from the preferred plane.

16. The bending forceps system according to claim 15, including second counter bearings and a second bending punch wherein the first counter bearings and the first bending punch are designed for bending in the preferred plane, and the second counter bearings and the second bending punch are designed for bending outwardly from the preferred plane.

17. The bending forceps system according to claim 1, wherein the first bending punch is contoured in order to co-operate with a complementary contour of the surgical element.

18. The bending forceps system according to claim 1, wherein the first counter bearings and the first bending punch are contoured in order to co-operate with a complementary contour of the surgical element.

* * * * *